Figure 1:
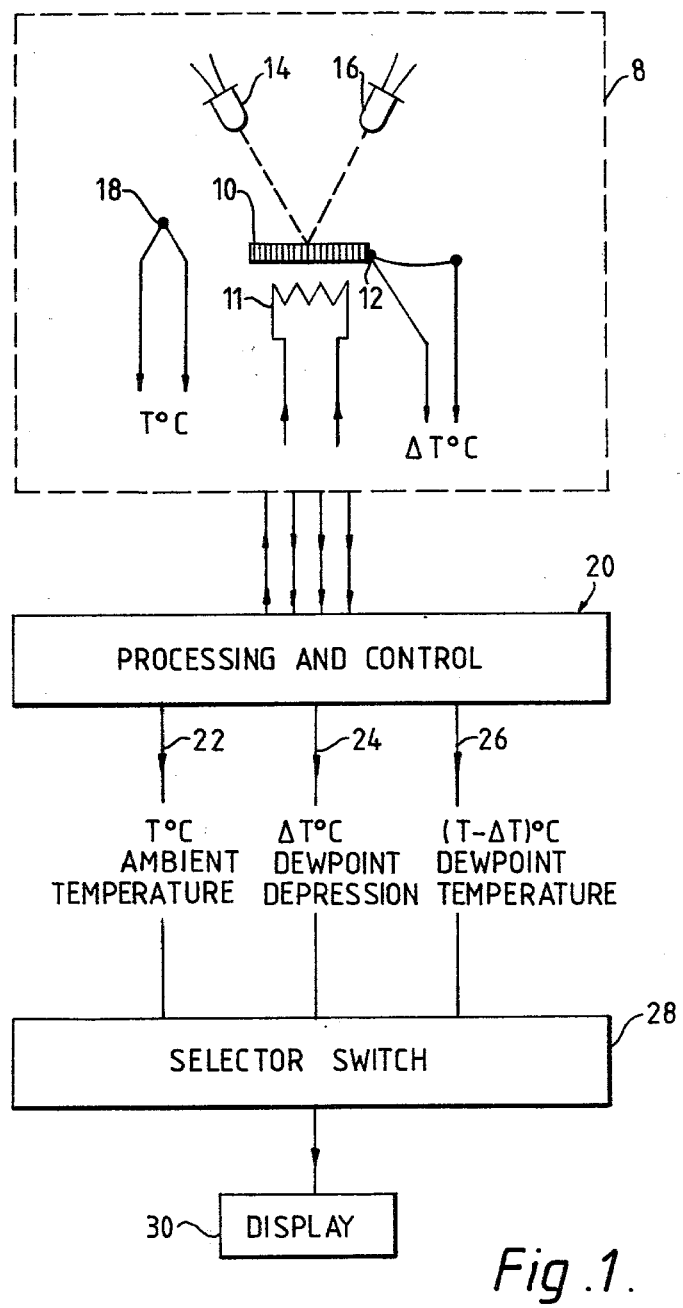

United States Patent [19]

Dadachanji

[11] 4,276,768

[45] Jul. 7, 1981

[54] RELATES TO APPARATUS FOR MEASURING THE DEW POINT

[76] Inventor: Fali M. Dadachanji, 32 Highfield Park, Marlow, Buckinghamshire, England

[21] Appl. No.: 95,105

[22] Filed: Nov. 16, 1979

[30] Foreign Application Priority Data

Nov. 22, 1978 [GB] United Kingdom ............ 45674/78

[51] Int. Cl.$^3$ ......................................... G01N 25/68
[52] U.S. Cl. ................................................. 73/17 A
[58] Field of Search ...................................... 73/17 A

[56] References Cited

U.S. PATENT DOCUMENTS

| | | | |
|---|---|---|---|
| 3,195,344 | 7/1965 | Francisco | 73/17 A |
| 3,204,418 | 9/1965 | Mathews | 73/17 A |
| 3,664,177 | 5/1972 | Bridgeman et al. | 73/17 A |
| 3,926,052 | 12/1975 | Bechtel | 73/17 A |

*Primary Examiner*—Donald O. Woodiel
*Attorney, Agent, or Firm*—Shlesinger, Fitzsimmons & Shlesinger

[57] ABSTRACT

There is disclosed apparatus for measuring the dew point which is arranged to carry out a method in which there is repeatedly performed a measuring cycle in which a body on which dew can form is cooled gradually until the formation of dew thereon is detected by detecting means, the temperature at which dew forms on said body being recorded in the apparatus and the temperature of said body being subsequently allowed to rise prior to cooling again in the next succeeding cycle. The temperature of said body is monitored continuously and the rate of cooling of the body in each cycle is controlled in dependence upon the difference between the instantaneous temperature of said body and the dew point temperature measured in a preceding cycle and recorded in the apparatus, in such a way that the rate of cooling is lower for at least a range of temperatures closer to said dew point temperature recorded in said previous cycle than for instantaneous temperatures of said body further from said dew point temperature recorded in said previous cycle. Thus, it is possible to combine the advantages of a rapid cooling rate, affording a high sampling frequency, and of a slow cooling rate, affording good accuracy.

5 Claims, 5 Drawing Figures

RELATES TO APPARATUS FOR MEASURING THE DEW POINT

This invention relates to apparatus for measuring the dew point.

Various forms of apparatus are known for measuring the dew point, including electrically operated apparatus arranged to effect at least part of the measuring process automatically. Known dew point measuring apparatuses of the last noted type generally operate by one of two methods.

In the first such method a body having an optically smooth surface is kept continuously substantially at the dew point by means of a thermo-electric cooling means controlled by a signal derived from a light sensitive element such as a photocell arranged to detect the scattering from the smooth surface of light from a light beam directed onto said surface, said scattering resulting from the formation of dew on said surface, the arrangement being such that the amount of dew on said surface is maintained at a substantially constant predetermined level by corresponding regulation of the temperature so that the temperature of said surface is maintained continuously at the dew point.

In the second of the two methods referred to, a body having an optically smooth surface is cooled thermo-electrically from a temperature above the dew point, the temperature of the surface being monitored continuously, a beam of light being again directed on to said surface and the formation of dew thereon being again detected by the consequent scattering of light from said surface, the temperature at which the degree of such scattering reaches a predetermined level being taken as a measure of the dew point temperature. Where continuous monitoring of the dew point is required, the body providing the optically smooth surface is allowed to rise above the dew point temperature one more each time it has been cooled below this temperature and the cycle repeated continuously so that the dew point temperature is effectively sampled at regular intervals.

In the first noted method, continuous monitoring of the dew point temperature is provided automatically.

The first of the two methods noted has the disadvantage of requiring more power than the second method, (this power being required to maintain the body providing the smooth surface continuously at a low temperature), the dissipation of this power giving rise inevitably to the generation of heat elsewhere in the apparatus, and thus at a location fairly close to the body being cooled, and this circumstance may give rise to errors unless complex ventilation arrangements are resorted to to achieve thermal equilibrium.

The second of the two methods discussed affords the inherent disadvantage that the frequency at which samples of dew point temperature are provided is lower the higher the accuracy required since, if the earliest possible detection of dew formation on the surface is to be achieved and errors due to time lag effects are to be avoided, it is necessary for the body providing the optically smooth surface to be cooled very slowly so that the duration of each sampling interval is correspondingly long and the sampling frequency correspondingly low.

It is an object of the present invention to provide an improved apparatus for measuring the dew point which is arranged to operate by a method which is essentially a variant of the second of the two methods noted but which minimises the disadvantages of the latter method.

According to the invention there is provided apparatus for measuring the dew point comprising a body having associated therewith means for sensing the formation of dew on said body, means for cooling said body, and means for sensing the temperature of said body, the apparatus further comprising control means arranged to cause the apparatus to perform repeatedly a cycle in which said body is cooled gradually until the formation of dew thereon is detected, a temperature at which dew forms on said body being recorded in the apparatus and the temperature of said body being subsequently allowed to rise prior to cooling again in the next succeeding cycle, the temperature of said body being monitored continuously and the rate of cooling of said body being controlled in dependence upon the difference between the instantaneous temperature of said body and the dew point temperature measured in a preceding cycle and recorded in the apparatus, in such a way that the rate of cooling is lower for at least a range of temperatures closer to said dew point temperature recorded in said previous cycle than for instantaneous temperatures of said body further from said dew point temperature recorded in said previous cycle.

Thus, it is possible to combine the advantages of a rapid cooling rate, affording a high sampling frequency, and of a slow cooling rate, affording good accuracy.

Preferably the arrangement is such that when dew formation is detected in each cycle, the corresponding dew point temperature is recorded in the apparatus and serves as the recorded dew point temperature with which the instantaneous temperature is compared in the succeeding cycle to determine the cooling rates at the various stages in the succeeding cycle. Thus the dew point temperature recorded in the apparatus is updated at every cycle.

Preferably said body has an optically smooth surface, and the means for sensing the formation of dew on said surface of the body includes means for directing a beam of light onto said surface and means for detecting the scattering of light from said surface due to the formation of dew thereon.

However, the formation of dew may, if desired, be detected by some other method, for example by sensing the electrical resistance between two points on the surface of the body, as noted hereinafter with reference to FIG. 5 of the accompanying drawings.

Figure 2:
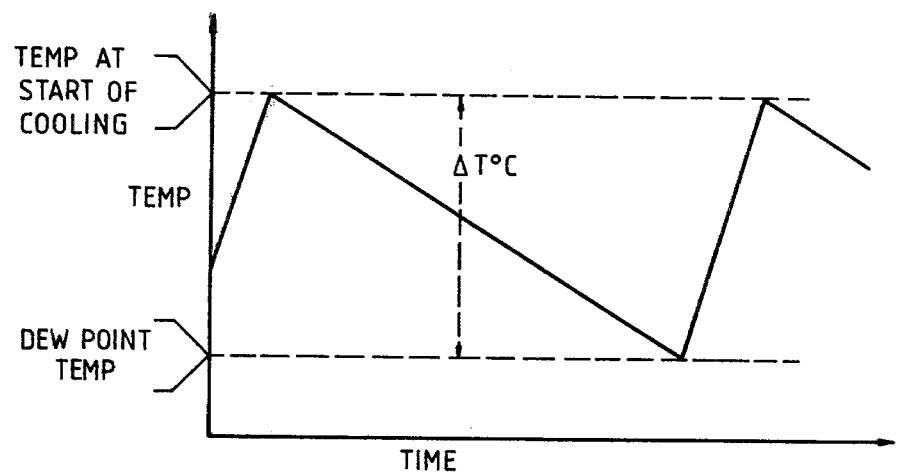
Figure 3:
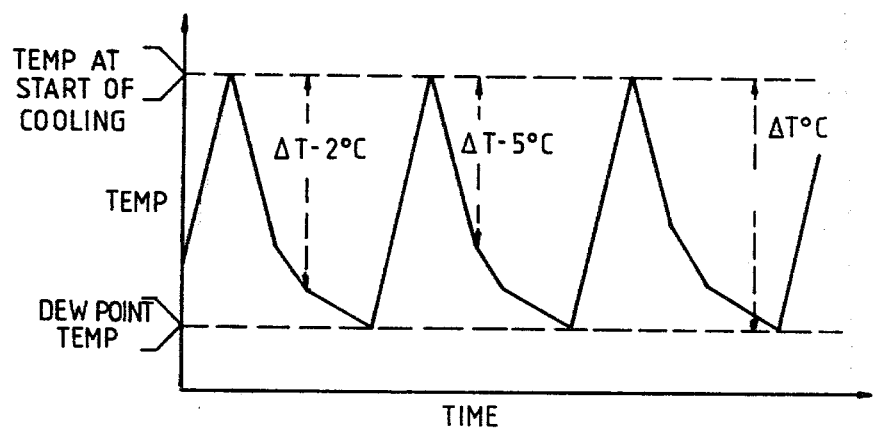
Figure 4:
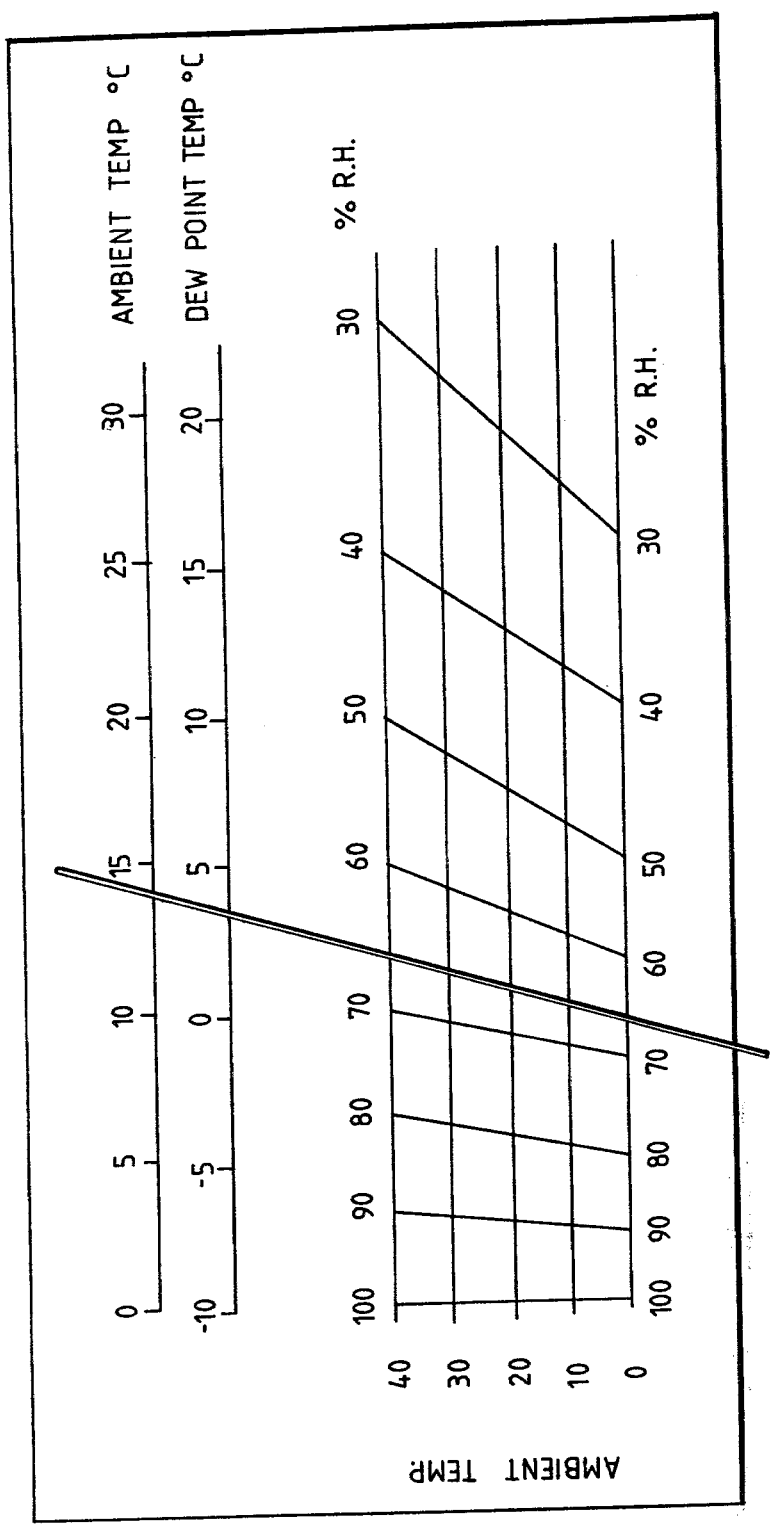
Figure 5:
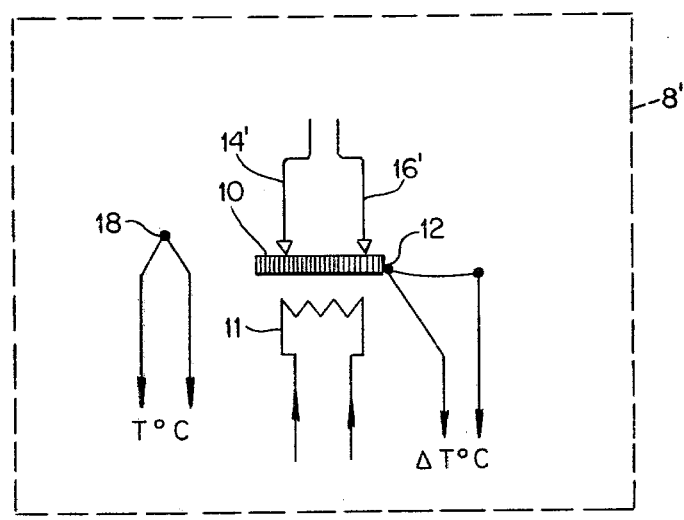

A preferred embodiment of the invention is described below with reference to the accompanying drawings in which:

FIG. 1 is a schematic diagram of an apparatus embodying the invention,

FIG. 2 is a graph showing a single cycle of a conventional dew-point measuring apparatus operating by the second known method referred to above, FIG. 3 is a graph similar to FIG. 2 and to the same scales but showing the operation of the apparatus of FIG. 1, FIG. 4 shows a meter dial which may be used in the apparatus of FIG. 1; and FIG. 5 is a schematic diagram of a modified form of the sensor shown in FIG. 1.

Referring to FIG. 1, the apparatus includes sensor 8 which incorporates a body 10, for example of metal, providing an optically smooth reflective surface, the body 10 having associated therewith cooling means 11, for example thermo-electric cooling means operating by the Peltier effect, and also having associated therewith a temperature sensing device 12, such as a thermistor, or thermocouple in contact with or embedded in the body 10. A light source 14 is arranged to direct a beam of light on to said reflective surface of the body 10 and an electrical photo-sensitive device 16, such as a photocell, photo-diode or the like is arranged to receive the light, from the light source 14, after reflection by the reflective surface of body 10. A further temperature sensing device 18, such as a thermistor or thermocouple, is provided for sensing the ambient temperature.

The cooling device, the device 12, 18, the light source 14 and the photosensitive device 16 are electrically connected with circuitry indicated generally at 20 for supplying the necessary electrical current to the cooling means 11 and the light source 14 and receiving and processing the electrical signals from the thermistors and the photosensitive device 16, the circuitry 20 also being arranged to provide respective output signals on respective outputs 22, 24, 26 which are selectively connectable, by a manually operable selector switch 28 with a display device 30, such as a galvanometer, arranged to indicate the results of the measurements effected.

The circuitry 20, selector switch 28 and display 30 are preferably mounted in a suitable casing, (not shown), and the sensor 8 may be formed separately from this casing and connected with the circuitry 20 in said casing via suitable flexible cables so that the sensor 8 can be disposed at locations remote from the casing housing the circuitry 20.

In operation of the apparatus, the body 10 is cooled gradually below ambient temperature by operation of the cooling means until a predetermined change in the level of light detected by the device 16 and thus in the electrical output signal from device 16, is detected, said change being due to the formation of dew on the reflective surface of the body 10. During cooling of the body 10, the temperature thereof is continuously monitored by means of the device 12 and the temperature of the body 10, at the time when said predetermined change in the level of light reflected from body 10 is attained, is recorded in the circuitry 20 as the dew point temperature measured in that cycle. The body 10 is then allowed to rise in temperature once more, or may even be caused to do so by deliberately heating the body 10 to some extent, whereafter the entire cycle is repeated, the body 10 being again gradually cooled until the formation of dew thereon is detected.

However, whereas in the known dew point measuring apparatuses referred to above, operating by the second of the known methods referred to, the body on which dew is to be formed is cooled at a substantially uniform rate, in the embodiment under discussion, the rate of cooling is varied in accordance with the difference between the instantaneous temperature of the body 10 and the dew point temperature sensed in the preceding cycle and recorded in the circuitry 20. Thus, when the difference between the temperature of body 10 and the dew point temperature sensed in the previous cycle is greater than a first predetermined amount, which amount may, for example, be between 4 and 6 Celsius degrees, the cooling of the body 10 is effected at a first, rapid cooling rate, whereas when the difference between the instantaneous temperature of the body 10 and the dew point temperature sensed in the previous cycle is less than said first predetermined amount but greater than a second predetermined amount, (which second predetermined amount may, for example, be between 2 and 4 Celsius degrees) the body 10 is cooled at a second predetermined rate substantially less rapid than said first predetermined rate and when the difference between the instantaneous temperature of the body 10 and the dew point temperature sensed in the previous cycle is less than said second predetermined amount, the body 10 is cooled at a third predetermined rate substantially less than said second predetermined rate, so that in the temperature range where the dew point is likely to be in the current cycle the rate of change of the temperature of the body 10 is slow, thus allowing maximum accuracy to be obtained. When, in each cycle, the dew point is attained, the dew point temperature is recorded in place of that previously recorded, so that the apparatus is updated in each cycle.

The circuitry 20 includes means for receiving the signals from the devices 18 and 12 and the photosensitive device 16, amplifying the same as necessary, in particular the signal from the device 16, threshold circuitry for detecting a change in the signal from device 16 significant of dew formation, recording means for recording the temperature of body 10 at the instant that dew formation is detected and means for providing at the outputs 22, 24, and 26 respectively appropriate output signals corresponding to the ambient temperature sensed by device 18, the dew point depression temperature (which is the temperature difference between ambient temperature and the dew point temperature), and the dew point temperature itself. The circuitry 20 also includes circuitry for controlling the current through the cooling means 11 in accordance with the determined difference between the instantaneous temperature of body 10 and sequencing circuitry operable to ensure that the apparatus performs repeating cycles in the manner indicated.

FIG. 3 illustrates the manner in which the temperature of the body 10 varies over a number of cycles, for the case where said second predetermined cooling rate is applied for a difference of 5 Celsius degrees between the instantaneous temperature of the body 10 and the dew point temperature sensed in the previous cycle and said third predetermined cooling rate is applied for a difference of less than 2° between the instantaneous temperature of the body 10 and the dew point temperature sensed in the preceding scale.

In FIG. 3, surface temperature of body 10 is plotted along the ordinate and time elapsed is plotted along the abcissa. The different cooling rates applied are clearly evident. As illustrated in FIG. 3, after the dew point is reached in each cycle, the body 10 is returned each time to the same initial temperature, above the dew point, before commencing the next cycle.

By way of comparison, FIG. 2, shows a similar graph, in which the scales on the ordinate and abcissa are the same as in FIG. 3, but relating to the known apparatus referred to above operating by the second of the known methods previously referred to. FIG. 2 illustrates the variation of the surface temperature of the body on which dew is to be formed during a single sensing cycle, the body providing said surface being cooled at a rate equal to the third and smallest predetermined rate in the examples shown in FIG. 3, in order to achieve the same accuracy of measurement. It will be noted that a single sensing cycle in the prior art example of FIG. 2 occupies the same time as several cycles in the example of FIG. 3.

It will be appreciated that the circuitry 20 may be wholly analog in nature, or partly digital in operation, so that, for example, where the circuitry is partly digital, the dew point temperature sensed may be recorded in digital form in a digital register, and the circuitry whereby the dew point depression temperature is calculated may also operate digitally, while the display may be a digital display. Where the circuitry 20 is wholly analog in operation, the dew point temperature sensed may be recorded in analog form as a charge on a capacitor, for example and analog computing techniques may be used for signal processing, the display taking the form of a galvanometer. In the embodiment illustrated it is assumed that the circuitry 20 operates in analog fashion and that the display device 30 is a galvanometer.

FIG. 4 illustrates the scale of such a galvanometer. As the relative humidity is a function of dew point depression temperature and ambient temperature, relative humidity (% RH) can also be displayed on the same dial as a function of the ambient temperature, as illustrated. It will be appreciated that, particularly where digital techniques are employed, computation of the relative humidity may be effected within the instrument, using analog or digital techniques rather than mentally with the assistance of the dial.

It will be appreciated that a wide variety of variations may be made within the scope of the invention. Thus, for example, whilst in the example indicated both the ambient temperature and the temperature of body 10 are sensed directly and the difference between them at the dew point calculated, it is possible to measure directly, for example, the ambient temperature and the difference between the ambient temperature and that of body 10, the actual temperature of body 10, if desired, being reached by calculation.

Similarly, it will be appreciated that whereas in the example given three cooling rates are provided, only two may be provided in certain instances, while four or more may be provided in others, or the cooling rate made variable continuously as a function of the difference between the previously sensed dew point temperature and the instantaneous temperature of body 10.

Moreover, as noted above, a modified sensor of the type denoted at 8' in FIG. 5 may be employed, utilizing instead of the light source 14 and photodetector 16 conventional means such as probes 14' and 16' for sensing the electrical resistance between two points on the surface of the body 10.

I claim:

1. Apparatus for measuring the dew point, comprising a body on which dew can form, cooling means for cooling said body, dew-sensing means for sensing the formation of dew on said body, temperature sensing means for sensing the temperature of said body, and control means including recording means, said control means being operable to cause the apparatus to perform repeatedly a cycle in which said body is cooled gradually until the formation of dew thereon is detected, the temperature at which dew forms on said body is recorded by said recording means, and the temperature of said body is subsequently allowed to rise prior to cooling again in the next succeeding cycle, the temperature of said body being monitored continuously by said temperature sensing means and the rate of cooling of said body being controlled by said control means in dependence upon the difference between the instantaneous temperature of said body and the dew point temperature measured in a preceding cycle and recorded by said recording means, in such a way that the rate of cooling is lower for at least a range of temperatures closer to said dew point temperature recorded in said previous cycle than for instantaneous temperatures of said body further from said dew point temperature recorded in said previous cycle.

2. Apparatus according to claim 1 which is operable to record, by said recording means, the temperature of said body at which the formation of dew is detected in each cycle, the control means being operable to utilise the temperature so recorded as the recorded dew-point temperature with which the instantaneous temperature is compared in the succeeding cycle to determine the cooling rates at the various stages in said succeeding cycle, whereby the dew-point temperature recorded in the apparatus is up-dated at every cycle.

3. The apparatus of claim 1 wherein said body has an optically smooth surface, and said means for sensing the formation of dew on said surface of the body includes light-directing means for directing a beam of light on to said surface, and means for detecting the scattering of light from said surface due to the formation of dew thereon.

4. The apparatus of claim 1 wherein said means for sensing the formation of dew on said body comprises means for sensing the electrical resistance between two points on the surface of the body.

5. A method of measuring the dew point comprising providing a body having associated therewith means for sensing the formation of dew on said body, and means for sensing the temperature of said body, and repeatedly performing a cycle in which said body is cooled gradually until the formation of dew thereon is detected, the temperature at which dew forms on said body is recorded and the temperature of said body is subsequently allowed to rise prior to cooling again in the next succeeding cycle, the method further including monitoring the temperature of said body continuously and controlling the rate of cooling of said body in dependence upon the difference between the instantaneous temperature of said body and the dew point temperature measured and recorded in a preceding cycle, in such a way that the rate of cooling is lower for at least a range of temperatures closer to said dew point temperature recorded in said previous cycle than for instantaneous temperatures of said body further from said dew point temperature recorded in said previous cycle.

* * * * *

UNITED STATES PATENT OFFICE
CERTIFICATE OF CORRECTION

Patent No. 4,276,768  Dated July 7, 1981

Inventor(s) Fali Minocher Dadachanji

It is certified that error appears in the above-identified patent and that said Letters Patent are hereby corrected as shown below:

On the title page, after the inventor's name and address insert the following paragraph:

--[73] Assignee: Protimeter Limited, Buckinghamshire, England --.

Signed and Sealed this

Twenty-ninth Day of September 1981

[SEAL]

Attest:

Attesting Officer

GERALD J. MOSSINGHOFF

Commissioner of Patents and Trademarks